United States Patent [19]

Morrison

[11] Patent Number: 4,466,958
[45] Date of Patent: Aug. 21, 1984

[54] FOOD SUPPLEMENT

[76] Inventor: Lester M. Morrison, 7012 La Presa Dr., Los Angeles, Calif. 90028

[21] Appl. No.: 245,023

[22] Filed: Mar. 18, 1981

[51] Int. Cl.$^3$ .................... A61K 33/00; A61K 31/70; A61K 31/685

[52] U.S. Cl. .................................. 424/127; 424/180; 424/199

[58] Field of Search ....................... 424/127, 199, 180

[56] References Cited

PUBLICATIONS

Morrison et al., P.S.E.B.M. 1950, vol. 73, pp. 37 and 38.
Circulation vol. 2, p. 479 of Sep., 1950, Morrison et al.
Corr et al., "Modern Concepts of Cardiovascular Disease", Sep., 1979, No. 9, pp. 49–52.
Morrison, Folia Angiologica, vol. XXV, of 9/10/77 pp. 225–233.
Morrison et al., Journal of the International Academy of Preventive Medicine, vol. IV, No. 2, Winter, 1977, pp. 9–21.
Murata, Japanese Heart Journal, Apr., 1961, pp. 198–209.
Morrison et al., Angiology, vol. 24, No. 5, May, 1972, pp. 269–287.
JAMA, Jan. 27, 1945, vol. 231, No. 4, pp. 360–381.
Morrison et al., Pro. Soc. Exper. Bio. and Med., 69:283–284 1948.
Morrison, Geriatrics, vol. 13, pp. 12–19, 1958.
Day, Atherosclerosis, 25 (1976) pp. 199–204.
Schwartz, Proceedings of the National Academy of Sciences, vol. 70, No. 5, pp. 1608–1612, May, 1973.
Schwartz, The Lancet, Feb. 26, 1977, pp. 454–457.
Morrison et al., Annals of Internal Medicine, vol. 37, No. 6, 1952, pp. 1172–1180.
Morrison, Journal of the American Medical Association, Dec. 10, 1955, vol. 159, pp. 1425–1428.
Izuku et al., Atherosclerosis, 1972, vol. 16, pp. 217–224.
Morrison, JAMA Jun. 25, 1960, pp. 884–888.
Morrison et al., "Coronary Heart Disease", Jul. 1982 by Karger A. G. of Basel, Switzerland.

*Primary Examiner*—Sam Rosen
*Attorney, Agent, or Firm*—Beehler, Pavitt, Siegemund, Jagger & Martella

[57] ABSTRACT

A novel food supplement containing phosphatidyl choline, phosphatidyl inositol and/or phosphatidyl ethanolamine, lecithin, a mucopolysaccaride, niacin and silicon dioxide, silicic acid and/or organic esters of silicic acid.

9 Claims, No Drawings

FOOD SUPPLEMENT

BACKGROUND OF THE INVENTION

Prior studies have shown that patients receiving phosphatidyl choline experienced a reduction by one-third of the death rate in recovered myocardial infarction cases over a three-year period of time. The anti-antherogenic properties of choline in experimental animals has also been shown. Although not as extensive as the choline studies, it has been found also that phosphatidyl inositol and lecithin demonstrated anti-atherosclerosis and blood plasma or serum liquid lowering efficacy.

Another study demonstrated the "clearing" effect of the phosphatidyl choline upon human coronary, aortic and other connective tissue cells in tissue culture systems. The "clearing" effects of this phosphatidyl choline was demonstrated by the removal of lipids such as cholesterol, beta lipoproteins, triglycerides and related lipoproteins from the arterial tissues of human origin.

Heparatin sulfate has been reported by two groups of investigators as having a significant anti-atherogenic property.

The effectiveness of crude, bovine trachael cartilage for prevention of experimental animal coronary heart disease has been reported. The ingredients in this crude extract include heparatin sulfate, keratan sulfate and chondroitin sulfate B, all mucopolysaccharides.

Silicon as a trace mineral has been reported as having anti-atherogenic properties.

Niacin or nicotinic acid has been demonstrated by numerous investigators in the scientific literature to possess lipid-lowering and anti-antherogenic activities. In a recent study by the National Institutes of Health entitled "The Coronary Drug Project Study", (JAMA, Vol. 231, No. 4, p. 360, Jan. 27, 1975), it was shown that nicotinic acid could reduce the heart attach rate by one-third.

It has also been reported that there was obtained a 74% to 80% clinical improvement in 134 patients with coronary heart disease, cerebral atherosclerosis such as "stroke", and peripheral, ischemic atherosclerotic obstruction of the lower extremities when such patients were treated with calf aorta extract comprising elastomucoproteases enzyme inhibitor.

Clinical improvement and blood cholesterol lowering effect of lecithin has also been described in patients with confirmed coronary heart disease.

The present invention relates to a novel and improved combination of ingredients. Although it is evident that most of the above-described individual ingredients in the combination of the invention have been reported in the scientific literature, no one has ever published such combinations, either in toto or in part for the purposes we employ. The synergy of the above combinations has been proven in the following ways including:

Marked reduction in death rate to zero from fatal myocardial infarction, stroke, and arteriosclerotic complications;

Amelioration of symptoms of angina pectoris;

Reduction in coronary thrombosis, coronary incidents, heart attacks, nonfatal heart attack;

Increase in exercise tolerance;

Increase in protective blood plasma parameters by lowering fibrinogen, cholesterol, triglycerides, beta lipoproteins, VLDL, LDL, ESR, and increasing the protective HDL; and Increase in well-being.

More generally, the novel combination of this invention shows the safety and efficacy against atherosclerotic complications of coronary artery disease, cerebrovascular disease such as stroke, peripheral ischemic obstructive athero-arteriosclerosis of the lower extremities, cerebrovascular symptoms such as dizziness (vertigo), and intermittent claudication (pains in legs while at rest or during walking), and related disorders.

SUMMARY OF THE INVENTION

Briefly, the present invention comprises a novel food supplement containing phosphatidyl choline, phosphatidyl insitol and/or phosphatidyl ethanolamine, lecithin, a mucopolysaccharide, niacin and silicon dioxide, silicic acid and/or organic esters of silicic acid.

More particularly, the invention comprises a novel food supplement containing phosphatidyl choline, phosphatidyl insitol and/or phosphatidyl ethanolamine, lecithin, chondroitin sulfate B, heparatin sulfate, keratan sulfate, niacin and silicon dioxide, silicic acid and/or organic esters of silicic acid.

It is an object of this invention to provide a novel food supplement.

More particularly, it is an object of this invention to provide a new and more beneficial combination of ingredients which enhance longevity in cases of confirmed coronary artery heart disease.

These and other objects and advantages of this invention will be apparent from the detailed description which follows.

The preferred mucopolysaccharides, which serve as elastomucoproteases inhibitors, include:

Hyaluronic acid from
   (a) Human umbilical cord
   (b) Bovine vitreous humor

Chondroitin 4-sulfate from
   (c) Notocord of rock sturgeon
   (d) Rat costal cartilage
   (e) Mammalian nasal septal cartilage
   (f) Shark cartilage Chondroitin 6-sulfate from
   (g) Human umbilical cord
   (h) Human cartilage
   Sturgeon cartilage
   (j) Mammalian nasal septal cartilage
   (k) Shark cartilage Dermatan sulfate from
   (l) Hog mucosal tissue Heparan sulfate from
   (m) Beef lung Heparin from
   (n) Hog mucosal tissue Keratan sulfate-1 from
   (o) Bovine cornea Keratan sulfate-2 from
   (p) Human costal cartilage Chondroitin polysulfate Rice Paddy Bran Calf Aorta extract comprising, primarily, elastomucoproteases, enzyme inhibitor.

The silicon ingredient may be ordinarily silicon dioxide, erthosilicic acid, polysilicic acid, ethyl silicate or other similar compounds.

The lecithin normally contains various vitamins including Vitamin K along with phosphatidyl chloline and phosphatidyl inosoitol.

DESCRIPTION OF THE PREFERRED EMBODIMENTS

In the novel combination of this invention, the following general formulation is preferred:

|  |  | Weight % | Weight % |
|---|---|---|---|
| Phosphatidyl choline |  | 5–40 | 10% |
| Phosphatidyl inositol |  | 5–40 | 10% |
| Phosphatidyl ethanolamine |  | 5–40 | 10% |
| Soya lecithin |  | 5–60 | 28% |
| Chondroitin sulfate B | ⎫ | 5–40 | 10% |
| Heparatin Sulfate (heparan) | ⎪ | 5–40 | 10% |
| Keratan sulfate | ⎬ Mucopolysaccarides | 5–40 | 10% |
| Elastomucoproteases enzyme inhibitor | ⎭ | 0.2–10 | 6% |
| Silicon dioxide |  | 1–30 | 5% |
| Niacin |  | 0.1–2 | 1% |
|  |  |  | 100% |

In the combination, the essential ingredients are phosphatidyl choline, phosphatidyl inositol and/or phosphatidyl ethanolamine, soya lecithin, and one or more mucopolysaccarides. The other ingredients are optional and preferred.

The ingredients are typically in powdered form and are dry blended in a mixer. The mixture can then be packaged as a blended powder or formed into capsules, tablets, or into a liquid mixture as a drink, and the like.

The novel food supplement was tested in 66 patients suffering from severe, advanced coronary atherosclerotic heart disease (some even had undergone open-heart coronary bypass surgery) or atherosclerotic brain damage such as previous stroke or other cerebral symptoms, while others suffered from atherosclerotic obstructions of the arteries of the legs. Some patients were victims of combinations of more than one of the above conditions. Table I shows the comparision of results of treatment by the novel food supplement.

It is seen that no deaths occurred in the treatment group of 66 patients after three years of the above therapy, when supported by a low fat, low cholesterol diet. These results are quite striking when compared to those reported in the scientific, medical literature. The mortality rate in such comparable patients was found to range as a rule between 5 and 10% yearly. In other words, a three-year death rate in 66 advanced atherosclerotic coronary heart disease with or without the above additional atherosclerotic complications would conservatively be found at 5% annual mortality rate to be nine deaths (out of 66 patients) over a three-year period.

Although the comparison between 0 cardiac deaths with the novel food supplement and nine heart deaths from expected mortality is most striking, the remarkable relief from symptoms on the food supplement is also notable. As in the descriptions of the following investigations, patients found relief from angina (chest pains), shortness of breath, increased tolerance to exercise, walking, leg distress and work, dizzy spells and other commonly experienced circulatory distress. Most noted a marked sense of well being. These improvements in symptoms usually took an average of two to six weeks for the patient's body to assimilate and apply the nutrients ingested. The patients received an average dosage of about 16 grams of the food supplement daily.

TABLE I

COMPARISON OF MORTALITY FROM RECURRENT HEART ATTACKS DURING USE OF NOVEL FOOD SUPPLEMENT, THREE YEARS

|  | No. of Patients Novel Food Supplement 66 | No. of Patients Conventional Therapy 66 |
|---|---|---|
| Ages | Comparable | Comparable |
| Sex | Equal | Equal |
| Severity of Disease | Same | Same |
| Expected Morality Rate | 5"10% | 5–10%* |
| Yearly Death Rate | 0 | 3–6* |
| Total No. of Deaths after three years | 0 | 9–18* |

*From scientific literature for severe, advanced coronary heart disease (CHD).

In all these patients, extensive, objective laboratory blood tests, including blood chemistry analyses, six tests of the different types of blood lipids (including the four different types of beneficial and harmful forms of cholesterol, tests for functions of the liver, kidneys, thyroid and other blood systems such as blood clotting, etc.

All patients underwent electrocardiographic evaluation; in appropriate patients exercise tests were conducted on exercise tolerance by the walking treadmill electrocardiographic evaluations by specialists in this field. Also included were X-rays of the heart and in various patients coronary artery angiograms, echocardiograms of the heart, ultrasound cerebrovascular measurements (Doppler) and cerebrovascular angiograms were carried out.

The results obtained with the food supplement are most surprising when compared to the results obtained when only individual ingredients are ingested. A series of 115 patients were treated with phosphatidyl choline. These patients had proved coronary thrombosis indicated by typical serial electrocardiograms and clinical history; they had survived the acute episode of occlusion and were discharged from the hospital. A series of patients with similar proved coronary thrombosis who did not receive phosphatidyl choline treatment served as the control subjects since they were alternate unselected patients who had entered the hospital under the same conditions. These patients had survived their acute epoisode and were also discharged under the same conditions. The dosage which was first employed was aimed at a maximum of 32 grams daily by mouth, since the senior author as well as other investigators have shown that in experimental atherosclerosis the most effective therapeutic results in prevention or absorption of the atheromatous lesions are achieved when the maximal dose which the animal can tolerate is ingested. However, many patients were unable to take this dose of 32 grams daily for prolonged periods of time and a small percentage were unable to tolerate any amount of choline due to the ensuing gasteroenteritis. The minimum dosage taken was 6 grams daily of the phosphatidyl choline in the form of the bicarbonate salt, and the average oral dose for most patients was 12 grams daily. Occasional minor but unpleasant side reactions occurred—mostly manifestations of gastroenteritis, vertigo, or body odor.

The treated and the control patients have been treated in identical manner, with the currently used standard methods of bed rest, palliative therapy, morphine, a hospital select diet, and, in the past one and one-half years, routine administration of Dicumarol to every patient. After the patients were discharged from the hospital they either attended the special research clinic in the outpatient department of the hospital for choline treatment or they were observed as control patients who did not receive choline or who, in certain cases, were being treated in the cardiac or medical clinic by digitalis, low sodium diet, and other palliative medical therapy.

The ages of the patients treated with choline ranged from 28 to 70 with an average of 58 years. Those not treated with phosphatidyl choline ranged from 30 to 70 years. Of the 115 phosphatidyl choline-treated patients, 17 were female, 97 were male patients. Of the 115 non-choline-treated patients, 21 were female, 94 were male patients. Blood serum lipid studies including serum cholesterol and esters, phospholipids, esterases, total lipids, lipoprotein relationships, iodine metabolism, liver function tests, fat tolerance tests, and other studies were carried out for many years following the initial three-year study.

Of all phosphatidyl choline-treated and nontreated control patients, only those were included in the data who had had their first coronary occlusion, in order to avoid variable factors in the analysis.

The phosphatidyl choline-treated patients fell into three groups. Group 1 consisted of 52 patients who received phosphatidyl choline daily for one year. Group 2 consisted of 35 patients who received phosphatidyl choline daily for two years. Group 3 comprised 28 patients who took phosphatidyl choline daily for three years. Most of these patients took their daily dosage regularly except for occasional lapses of an unavoidable nature due to intercurrent noncardiac illnesses, employment or transportation difficulties, and the like.

Table III summarizes the mortalities of these patients who received phosphatidyl choline treatment after their discharge from the hospital following recovery. It is noted in Group I of Table II that four patients of the 52 under treatment died at the end of the first year following their hospital discharge for the initial attack of coronary thrombosis. Table III shows a comparison of the mortalities in 52 control subjects who did not receive phosphatidyl choline treatment. Ten of these patients died at the expiration of one year. Table II shows that 35 patients who received phosphatidyl choline for two years, three died at the end of one year as compared with seven deaths among 35 control patients who did not receive phosphatidyl choline and who were observed over the one-year period. Furthermore, in this same group of the phosphatidyl choline-tested patients, 32 survived in the second year; two of these patients died within the second year. In comparison, 28 patients of the nonphosphatidyl choline-treated patients survived in the second year from the original 35, and five of these had died at the expiration of the second year of observation.

A comparison is made of the total mortality rate in Table IV between the 115 phosphatidyl choline-treated patients with 14 deaths at the end of the three-year period and 115 nonphosphatidyl choline-treated subjects with 35 deaths at the end of the three-year observation period. This latter mortality rate in the nonphosphatidyl choline-treated series is comparable to those reported by previous observers.

TABLE II

SUBSEQUENT YEARLY SURVIVAL RATE IN 115 PATIENTS TREATED WITH PHOSPHATIDYL CHOLINE FOLLOWING A SIX-WEEK RECOVERY FROM ACUTE ATTACK OF CORONARY THROMBOSIS

| Group | Period of Observation (Years) | Number of Patients | Deaths During The Year |
|---|---|---|---|
| Group 1. | | | |
| One-Year Period of Phosphatidyl Choline Treatment | 1 | 52 | 4 |
| Group 2. | | | |
| Two-Year Period of Phosphatidyl Choline Treatment | 1 | 35 | 3 |
| | 2 | 32 | 2 |
| Group 3. | | | |
| Three-Year Period of Phosphatidyl Choline Treatment | 1 | 28 | 2 |
| | 2 | 26 | 2 |
| | 3 | 24 | 1 |

TABLE III

SUBSEQUENT YEARLY SURVIVAL RATE IN 115 NONPHOSPHATIDYL CHOLINE-TREATED CONTROL SUBJECTS FOLLOWING A SIX-WEEK RECOVERY FROM ACUTE ATTACK OF CORONARY THOMBOSIS

| Group | Period of Observation (Years) | Number of Patients | Deaths During The Year |
|---|---|---|---|
| Group 1, A. | | | |
| One-Year Period of Observation | 1 | 52 | 10 |
| Group 2, A. | | | |
| Two-Year Period of Observation | 1 | 35 | 7 |
| | 2 | 28 | 5 |
| Group 3, A. | | | |
| Three-Year Period of Observation | 1 | 28 | 5 |
| | 2 | 23 | 4 |
| | 3 | 19 | 4 |

TABLE IV

COMPARISON OF SURVIVAL RATES OF PATIENTS WITH CORONARY THROMBOSIS WITH AND WITHOUT PHOSPHATIDYL CHOLINE TREATMENT AFTER THREE YEARS

| Deaths in 115 Phosphatidyl Choline-Treated Patients: | 14 | Deaths in 115 Non-Phosphatidyl Choline-Treated Patients: | 35 |
|---|---|---|---|

LECITHIN RESULTS

In addition, the literature reports that in coronary patients receiving soya lecithin alone, or niacin alone, the death rate similarly is only reduced to less than one-third of normal.

Twenty-one hypercholesterolemic patients were treated with lecithin and their serum cholesterol and lipid responses were tested monthly for a three months' period.

All patients but two had previously followed a low-fat (25 gm.) daily dietry intake for periods ranging from one to ten years, but had failed to achieve any further lowering of serum cholesterol or lipid levels.

Each refractory case had previously been treated also with various cholesterol-lowering agents without further lowering of serum cholesterol or liquid levels.

All patients were given more than the customary amount of lecithin since they had proved resistant to previous diet and cholesterol-lowering agents. A dose of 2 tablespoonsful three times daily at meals was prescribed, or 35 gm. daily. Their previous low-fat diet was continued.

Six of 21 patients discontinued the lecithin because of intolerance to the large quantity taken, although smaller amounts of lecithin were well tolerated.

Of the 15 remaining patients studied, 12 showed a striking reduction of 41 percent in serum cholesterol levels, or an average fall of 156 mg. in three months following lecithin intake.

Three patients showed no significant fall in serum cholesterol or lipid intake. These three failed to respond, probably due to the introduction of steroid hormone therapy, increase in dietary fat intake, and induction of gastroenteritis during the lecithin study.

Twelve of the 15 patients showed an average of 129 mg. of total serum lipid fall after lecithin administration.

A therapeutically desirable relative increase in serum phospholipids with an increase in anti-atherogenic ration of phospholipid to cholesterol occurred in all patients following lecithin therapy.

NIACIN RESULTS

The rate of nonfatal or fatal heart attack was reported lower in a nicotinic acid group than a placebo group (25.6% vs. 30.1%, an apparent reduction in rate of 15%, Z value = −2.77). Atherosclerosis, 30 (1978) 239-242 and atherosclerosis 28 (1977) 81–86.

SILICON RESULTS

In the case of silicon compounds, it has been reported that there is an inverse relation between silicic acid in drinking water and the presence of heart disease in Finland. There is no reported quantified death rate study; *The Lancet*, Feb. 26, 1977.

MUCOPOLYSACCHARIDE RESULTS

The literature, *Z. Alternsforsch.* 34/2 (1979), S. 153-159, also reports that the effects of isomers of chondroitin sulfate on atherosclerosis were clinically compared, based on sulfate linkage and the amount of sulfate, by using chondroitin 4-sulfate, chondroitin 6-sulfate and chondroitin polysulfate. Forty-eight age-matched atherosclerotic subjects were selected from a home for the elderly in order to the treatment with the agents. The isomers of chondroitin sulfate were given a daily dose of 4.5 gm. perorally. During the experimental period for 64 months, mortality, serum cholesterol, thrombus-formation time and thrombus weight were examined.

The resulting data indicated that the isomers of chondroitin sulfate are clinically effective on the treatment of atherosclerosis in the order of chondroitin polysulfate, chondroitin 4-sulfate and/or chondroitin 6-sulfate.

Another clinical investigation was aimed to evaluate the effects of chondroitin polysulfate (CPS) on hyperlipemia with or without coronary heart disease by a peroral administration at a daily dose of 3.0 gram, three times after meals against lactate placebo controls. The study was carried out in the two systems: (1) in short-term study with a single crossover double blind system (8 weeks each) in 225 hyperlipemic subjects at multiinstitutional systems, and (2) in long-term study at the representative hospital in 40 patients for four years.

The results of lipid lowering effects by CPS indicated that the suppressions of both serum triglyceride and betalipoprotein (146 and 131 cases, respectively) were statistically significant ($p < 0.01$) by the administration of CPS.

On the other hand, serum nonesterified fatty acid (NEFA) was significantly increased ($p < 0.01$) in 47 cases by the treatment of CPS. The increasing rate by CPS was more marked in the cases showing lower initial values of NEFA than in those showing higher NEFA values.

No significant difference was observed in serum cholesterol (161 cases) by CPS administration when evaluation was made in the total numbers. A significant suppression in serum cholesterol by CPS was proved at a p value of 0.05 in an institute with 18 patients.

The long-term effects of CPS in 40 aged subjects for a period of four years showed that CPS prolonged significantly thrombus formation time and lowered serum lipid level. The mortality was less in the CPS treated group (7%) than the controls (21%).

The normal therapeutic dose of the food supplement is about one tablespoon or 8 grams per day. A preferred prophalactic dose is about 4 grams per day which can be most conveniently taken in the form of two 1-gram tablets, twice per day. In severe cases involving confirmed advanced cases of coronary disease and/or stroke, the dosage level is preferably about 2 to 4 tablespoons per day or about 16 to 32 grams per day.

The foregoing data include that the individual ingredients of the novel food supplement of this invention, when taken singly, do not have the same effect in lowering the mortality rate as does the food supplement.

Having fully described the invention, it is intended that it be limited only by the lawful scope of the appended claims.

I claim:

1. An improved food supplement for treating cardiac and circulatory difficulties containing effective amounts of phosphatidyl choline, phosphatidyl inositol and/or phosphatidyl ethanolamine, lecithin, a mucopolysaccaride, niacin and silicon dioxide, silicic acid and/or organic esters of silicic acid.

2. The food supplement of claim 1 wherein said mucopolysaccharide is selected from the group consisting of Chondroitin Sulfate B, heparan, Keratan sulfate and elastomucoproteases enzyme inhibitor.

3. The food supplement of claim 1 wherein said mucopolysaccharide is a mixture of Chondroitin Sulfate B, heparan, Keratan sulfate and elastomucoproteases enzyme inhibitor.

4. An improved food supplement for treating cardiac and circulatory difficulties comprising:

|  | Weight % |
|---|---|
| Phosphatidyl choline | 5–40 |
| Phosphatidyl inositol | 5–40 |
| Phosphatidyl ethanolamine | 5–40 |
| Soya lecithin | 5–60 |
| Chondroitin sulfate B | 5–40 |
| Heparatin sulfate | 5–40 |
| Keratan sulfate | 5–40 |
| Silicon dioxide | 1–30 |
| Niacin | 0.1–2 |

5. The method of improving health of a patient with cardiac or circulatory difficulty which comprises ingesting as part of the human diet a between 4 and 32 grams daily of a food supplement containing effective amounts of phosphatidyl choline, phosphatidyl inositol and/or phosphatidyl ethanolamine, lecithin, a mucopolysaccharide, niacin and silicon dioxide, silicic acid and/or organic esters of silicic acid.

6. The method of claim 5 wherein said mucopolysaccharide is selected from the group consisting of Chondroitin Sulfate B, heparan, Keratan sulfate and elastomucoproteases enzyme inhibitor.

7. The method of claim 5 wherein said mucopolysaccharide is a mixture of Chondroitin Sulfate B, heparan, Keratan sulfate and elastomucoproteases enzyme inhibitor.

8. The method of claim 5 additionally comprising:

|  | Weight % |
| --- | --- |
| Phosphatidyl choline | 5-40 |
| Phosphatidyl inositol | 5-40 |
| Phosphatidyl ethanolamine | 5-40 |
| Soya lecithin | 5-60 |
| Chondroitin sulfate B | 5-40 |
| Heparatin sulfate | 5-40 |
| Keratan sulfate | 5-40 |
| Silicon dioxide | 1-30 |
| Niacin | 0.1-2 |

9. An improved food supplement for treating cardiac and circulatory difficulties comprising:

|  | Weight % |
| --- | --- |
| Phosphatidyl choline | 10% |
| Phosphatidyl inositol | 10% |
| Phosphatidyl ethanolamine | 10% |
| Soya lecithin | 28% |
| Chondroitin sulfate B | 10% |
| Heparatin Sulfate (heparan) | 10% |
| Keratan sulfate | 10% |
| Elastomucoproteases enzyme inhibitor | 6% |
| Silicon dioxide | 5% |
| Niacin | 1% |
|  | 100% |

* * * * *